US00PP08612P

United States Patent [19]

Lamb et al.

[11] Patent Number: Plant 8,612

[45] Date of Patent: Feb. 22, 1994

[54] ANTHURIUM PLANT NAMED LOLLIPOP

[75] Inventors: Ann E. Lamb; Robert D. Hartman, both of Lake Placid, Fla.

[73] Assignee: Twyford International, Inc., Sebring, Fla.

[21] Appl. No.: 24,347

[22] Filed: Mar. 1, 1993

[51] Int. Cl.[5] ..... A01H 5/00

[52] U.S. Cl. ..... Plt./88.1

[58] Field of Search ..... Plt. 88.1

*Primary Examiner*—James R. Feyrer

*Attorney, Agent, or Firm*—Foley & Lardner

[57] ABSTRACT

An Anthurium plant named Lollipop having abundant red-pink flowers held above the foliage with a contrasting cream yellow spadix, a rounded symmetrical compact habit, very abundant branching, durable dark green shiny leaves, and tolerance to heat and the common disease Xanthomonas.

1 Drawing Sheet

1

The present invention comprises a new and distinct cultivar of Anthurium, botanically known as *Anthurium hybrid*, and referred to by the cultivar name Lollipop.

The new cultivar is a product of a planned breeding program carried out by the inventors Ann E. Lamb and Robert D. Hartman. The seedling is a result of a cross made between unidentified parents in Palmdale, Fla. The cultivar was discovered from the progeny of the stated cross by Ann E. Lamb. Propagation by tissue culture as performed at Palmdale, Fla., was used to increase the number of plants for evaluation and has demonstrated the stability of the combination of characteristics from generation to generation.

The following observations, measurements and values describe plants grown in Homestead, Fla. under shade house conditions which closely approximate those generally used in horticultural practice. The phenotype may vary somewhat with variations in environment such as temperature, light intensity and daylength, without, however, any variation in the genotype.

The following traits have been repeatedly observed to be characteristics which in combination distinguish Lollipop from other Anthuriums of the same general type, for example, the well known cultivar Lady Jane.

1. Intense red-pink blooms with contrasting yellow spadix.
2. The flowers are held above the leaf canopy.
3. The leaves are dark green, have a shiny surface, and are durable.
4. The plant habit is very compact and rounded.
5. The plant is very free branching.
6. The plant is heat tolerant.
7. The plant is field tolerant to Xanthomonas.

All color references are measured against The Royal Horticultural Society (RHS) Colour Chart. Colors are as true as reasonably possible with color reproductions of this type.

The drawing comprises a color photograph illustrating in top perspective view the inflorescence and foliage of Lollipop.

The plant of Lollipop illustrated was grown in a 25.5 cm pot and the photo was taken approximately 69 weeks after planting a 20 week old liner obtained by tissue culture and grown under appropriate growing conditions.

2

Origin: Seedling of unknown parentage.

Classification: Anthurium hybrid cv. Lollipop.

Propagation: Asexual production either by tissue culture or division.

Plant: In a 25.5 cm pot for a plant grown from a 20 week old liner after 69 weeks under appropriate growing conditions, a mature plant of Lollipop is approximately 28 cm to 37 cm in height and approximately 40 cm to 59 cm in width.

Leaves:

*Form.*—The leaf blade is deltoid with a cuspidate tip and a cordate base. The margins are entire. The midrib tends to curve downward over the length of the leaf. The leaf blade tends to be slightly wavy over the width of the leaf.

*Size.*—Leaf blades of a mature sized plant are approximately 15 cm to 17 cm in length and approximately 10 cm to 12.4 cm in width.

*Petiole.*—The petiole is approximately 10 cm to 13.5 cm in height from the base of the petiole to the base of the leaf blade on the primary shoot. Secondary shoots are somewhat smaller depending on the age of the shoot. The petiole is approximately 4 mm in diameter just below the geniculum. The petiole below the geniculum will be straight or slightly curved.

*Petiole wings.*—Petiole wings are approximately 2 cm in length and approximately 3 mm in width at their midpoint. The tips of the petiole wings are cordate. There is approximately 8.0 to 9.2 cm between the top of the wing and the base of the geniculum.

*Geniculum.*—The geniculum is approximately 20 mm to 23 mm in length, approximately 4.5 mm in diameter, and is often curved. The color is 144A-B. There is no space between the top of the geniculum and the base of the leaf blade. The geniculum is prominent.

*Veins.*—Veins are sunken, with the leaf blade slightly convex between veins on the upper surface. The midrib protrudes from the upper leaf surface of the leaf for approximately ⅔ the length of the leaf. Well defined primary veins on leaves radiate out from the juncture of the petiole and the leaf. Veins stand out prominently on the lower side. There are approximately 6 primary veins on the leaf.

*Lobes.*—The leaf has two lobes extending past the petiole. The distance from the petiole/leaf juncture to the highest point on the lobes is approximately 5.5 cm to 6.7 cm.

*Color.*—Upper surface: Lighter than 139A. Lower surface: 146C. Midrib, upper surface: 146C. Midrib, lower surface: 146D. Petiole: 144A-B. Petiole wing: 144B.

Inflorescence:

*Immature spathe.*—The spathe is tightly rolled around the spadix and extrudes from the petiole sheath. The spathe is fully open approximately when the pedicel is fully elongated, approximately 21 cm to 23.5 cm above the soil surface.

*Mature spathe.*—Size: The flattened spathe is approximately 4 cm to 6 cm long, approximately 4 cm to 5.5 cm in width, and 0.5 cm in depth-.Color, fully open: Upper surface: Pinker than 47B. Lower surface: Lighter than 47B. Color, faded: Upper surface: Lighter than 50B. Lower surface: 50B. Arrangement and shape: The spathe stands up on straight wiry pedicels and opens vertically above or among the leaves. The spathe is deltoid with a cordate base and a cuspidate apice that is straight. It is slightly cupped when first open but flattens and reflexes slightly as it ages. Flowering time: After approximately 16–18 months from a 20 week old liner for an untreated plant as illustrated and depending on season, approximately 10 to 12 blossoms will be present. Smaller blossoms may occur on less mature growth. First flowers can be expected approximately 4–5 months after planting a 20 week old liner. Approximately 1 to 3 flowers will be present.

Reproductive organs:

*Spadix.*—Approximately 2.5 cm to 4 cm in height and approximately 4 mm to 7 mm in width. Color: When the spathe unrolls, the spadix is 20C gradually changing to 145B before senescing. Stamens: Anthers and filaments are not clearly visible. Pollen: White in color. Pistil: Lighter than 20C in color, protruding between the staminate flowers, firmly fixed to the main axil. The pistilate flowers extend approximately 0.5 mm beyond the staminate flowes.

*Roots.*—White fleshy roots with fine laterals. Roots initiated above the soil have a light pink cast.

GENERAL OBSERVATIONS

Lollipop has abundant red pink flowers with a contrasting cream yellow spadix. The plant is very free flowering and very highly branched compared to other Anthuriums of this type, for example, Lady Jane. The leaves are dark green, shiny and durable. The plant habit is very compact and rounded. Lollipop is heat tolerant and field tolerant to the common greenhouse pathogen Xanthomonas. These combined characteristics make Lollipop a unique new cultivar.

I claim:

1. A new and distinct cultivar of Anthurium plant named Lollipop, as illustrated and described.

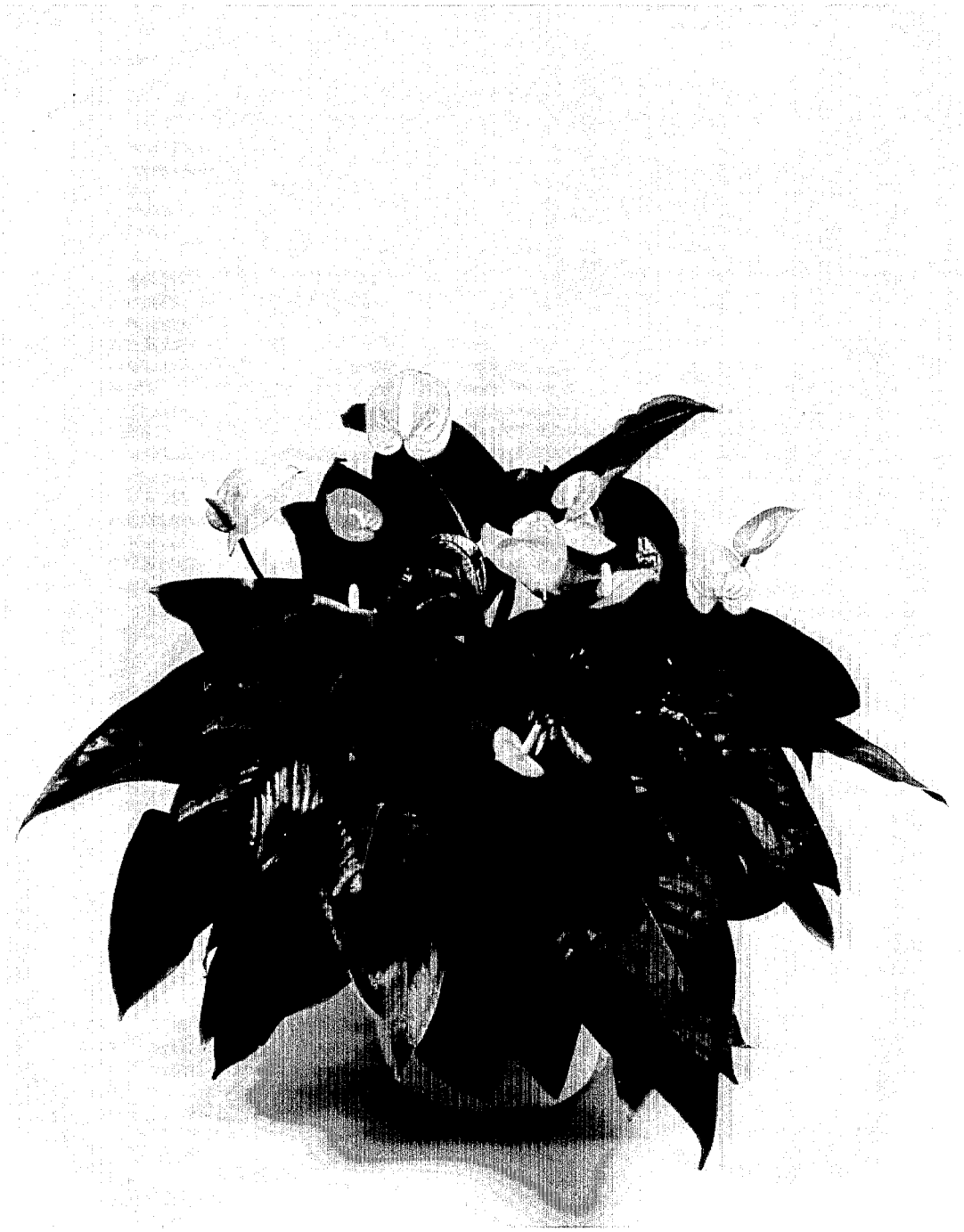

* * * * *